United States Patent [19]
Heine et al.

[11] 3,948,585
[45] Apr. 6, 1976

[54] OPHTHALMOSCOPE EXAMINATION PATTERN HAVING SLIT AND SURROUNDING RING

[75] Inventors: Helmut A. Heine, Herrsching, Upper Bavaria; Klaus Heilmann, Munich, both of Germany

[73] Assignees: Propper Manufacturing Company, Inc., Long Island, N.Y.; Optotechnik Heine KG, Germany

[22] Filed: June 20, 1974

[21] Appl. No.: 481,034

[30] Foreign Application Priority Data
Oct. 23, 1973 Germany............................ 2353121

[52] U.S. Cl. ........................ 351/13; 351/14; 351/16
[51] Int. Cl.² ............................................ A61B 3/12
[58] Field of Search .............................. 351/6, 9–12, 351/13, 14, 36, 7, 16

[56] References Cited
UNITED STATES PATENTS
| | | | |
|---|---|---|---|
| 1,613,658 | 1/1927 | Henker................................. | 351/14 |
| 2,110,330 | 3/1938 | Freeman............................... | 351/13 |
| 3,035,483 | 5/1962 | Andreas et al........................ | 351/12 |

*Primary Examiner*—Paul A. Sacher
*Attorney, Agent, or Firm*—Amster & Rothstein

[57] ABSTRACT

The present application discloses an examination pattern for use in conjunction with ophthalmoscopes which provide a illuminated slit surrounded by an illuminated ring to permit the physician to view the environment of the portion of the retina illuminated by the slit.

2 Claims, 2 Drawing Figures

OPHTHALMOSCOPE EXAMINATION PATTERN HAVING SLIT AND SURROUNDING RING

The invention concerns a radiant field stop, especially for ophthalmoscopes.

Ophthalmoscopes primarily serve to examine the rear of the eye; they are constructed to permit simultaneous illumination and observation of the field to be examined. The usual ophthalmoscope design has in its illumination path a light source, an aperture, an objective lens, and a deflection mirror which directs light towards the eye to be examined. On the examination side turned away from the patient, there is an observation window. This window allows the examining physician to make his observations by looking above the upper edge of the deflection mirror, or by looking through this mirror, if it is designed as a semi-transparent mirror.

For simple examination of the rear of the eye, the radiant light stop is designed as a simple circular aperture. For special diagnostic tasks, for example to determine level differences on the retina, to determine special structures of the retina, for example the formation of edemas, to measure distances along the rear of the eye, for example measurement of the diameters of retinal vessels, or for fixation tests, special radiant light stops can be provided. These are suitably so arranged that rapid switching from one stop to another is possible during examination. This can, for example, be realized by mounting different radiant light stops on a common aperture wheel, which can be adjusted from the outside.

Especially for determining level differences and pathological changes in the retinal surface, it is suitable and necessary to work with slit illumination. This slit illumination is achieved in such a manner that a slit-shaped radiant field stop is distinctly imaged on the rear of the patient's eye, through a suitably imaging objective, and taking into consideration the eye's own effective optical elements. Many diagnostic tasks require use of a very narrow slit. The illumination intensity of the slit image projected onto the rear of the eye cannot be made arbitrarily large, especially with hand ophthalmoscopes. The reason for this is the limited light power of the light sources used, as well as physiological considerations. Consequently, when such very narrow slits are used (the width of the slit image on the rear of the eye may be, for example, smaller than 0.05 mm), the examiner practically sees only the very small area illuminated by the slit, without being able to ascertain the neighborhood around the slit.

This poses serious difficulties for examination with slit illumination, since the examiner finds it difficult and often impossible to orient himself on the rear surface of the eye under investigation.

The invention is based on the task to make possible a slit illumination of the rear of the eye, which has a slit image of sufficiently narrow breadth, so as to be fully adequate for purposes of examination, but which on the other hand offers adequate capability for orientation on the rear of the eye under examination. This task is solved according to the invention by using a slit aperture to produce the slit image, and by arranging a light-transparent ring around this aperture. The slit aperture preferably runs along a diameter of the ring-shaped aperture.

The ring-shaped portion of the slit aperture, according to the invention, produces general illumination on the rear of the eye, because the area to be illuminated is very large compared to the slit. This enables the examiner to orient himself comfortably, without disturbing the slit image. This arrangement greatly facilitates performing such examinations on the rear of the eye, and is the first to provide the opportunity for applying this examination method in many cases.

In ophthalmoscopes with the ability of imaging the radiant light stop at various distances, the slit aperture can advantageously be also used to examine the optical elements of the eye, that is the cornea, the anterior chamber, the lens, and the vitreous body. Environmental illumination through the circular portion of the stop has no significance here, but a very narrow slit is again presupposed precisely in using slit illumination, if useful results are to be attained.

As already mentioned, a very narrow slit is applicable for investigating the rear of the eye only when the ring-field illumination, according to the invention, is available. Consequently, the arrangement according to the invention is likewise extraordinarily valuable for examining the optical elements of the eye, for which narrow slit widths are necessary.

The invention will be more fully appreciated by reference to the following detailed description of a presently preferred embodiment thereof, when taken in combination with the appended drawings, wherein.

Figure 1:
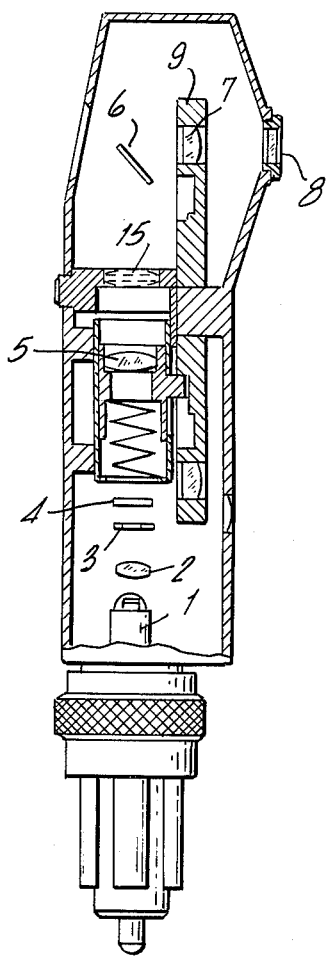
FIG. 1 shows the head of an ophthalmoscope in vertical section.

The ophthalmoscope of the presently preferred embodiment shown in FIG. 1 is described in greater detail in my U.S. Pat. No. 3,776,619 and has an incandescent lamp 1 as light source, which is fed from a battery or a cable connection (not shown). The radiant field stop or examination pattern forming mask 3 is illuminated through a condensor 2. Further, color or polarization filters 4 are provided.

An illumination objective 5 is mechanically coupled to a lens wheel (rekoss disk), and is movable along the optic axis. It images the radiant field stops, if necessary via an additional lens 15, at a distance which depends on the focal length of objective lens 5 and on the distance from the radiant field stop 3. The above-mentioned mechanical coupling with the rekoss disk can here be so designed that the setting of rekoss disk 9 is so related to the distance of objective lens 5, that a sharp image is assured on the rear of the patient's eye whenever the rear of the eye is sharply visible to the examiner. The illuminating beam is deflected onto the patient's eye by means of mirror 6. A number of lenses 7 is situated on rekoss disk 9, and these lenses have suitably graded focal lengths. The lens with the required focal length can be switched onto the path of the observation beam by turning this lens wheel. View opening 8 can be sealed by a plane disk or by a correcting lens.

Figure 2:
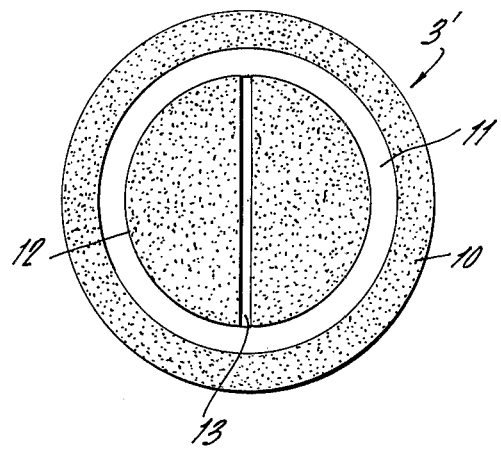
FIG. 2 shows a top view of a radiant field stop according to the invention.

FIG. 2 shows an embodiment of the radiant field stop 3'. The radiant field stop consists of an opaque outer ring 10, with a transparent ring 11 radially inward from the opaque ring. To this is attached an opaque circular disk 12, containing a slit 13, which runs through the midpoint of the circular rings. The width of slit 13 is 0.05 mm, in one exemplary embodiment, and the diameter of the opaque circular disk 8 is 1.8 mm. The width of the transparent ring 11 is about 0.15 mm.

What is claimed is:

1. An ophthalmoscope comprising means for projecting a beam of light into the eye of a patient and onto the fundus of the eye and shaping means for forming an examination pattern in said beam for projection onto said fundus, said shaping means including a non-light transmissive pattern forming mask having a light transmissive ring portion and a light transmissive slit portion which lies within and is enclosed by said ring portion.

2. Apparatus in accordance with claim 1 wherein said slit portion runs through the mid point of said ring portion.

* * * * *